United States Patent [19]
Miyake et al.

[11] Patent Number: 5,417,681
[45] Date of Patent: May 23, 1995

[54] MEDICAL CONTAINER DEVICE AND METHOD FOR MANUFACTURING SAME

[75] Inventors: Makoto Miyake; Noboru Ishida, both of Fujinomiya, Japan

[73] Assignee: Terumo Kabushiki Kaisha, Tokyo, Japan

[21] Appl. No.: 974,163

[22] Filed: Nov. 10, 1992

[30] Foreign Application Priority Data

Nov. 11, 1991 [JP] Japan .................................. 3-322507

[51] Int. Cl.⁶ .............................................. A61J 1/10
[52] U.S. Cl. .................................... 604/410; 604/403; 604/408
[58] Field of Search ................ 604/403, 408, 410, 416

[56] References Cited
U.S. PATENT DOCUMENTS

| | | |
|---|---|---|
| 4,222,379 | 9/1980 | Smith . |
| 4,223,675 | 9/1980 | Williams . |
| 4,332,122 | 6/1982 | Williams . |
| 4,369,779 | 1/1983 | Spencer . |

*Primary Examiner*—Corrine Maglione
*Attorney, Agent, or Firm*—Frishauf, Holtz, Goodman & Woodward

[57] ABSTRACT

A container device comprises a blood-collecting bag, a platelet conserving bag, and a plasma bag. These bags are connected each other by tubes. Anticoagulant agent is contained in the blood-collecting bag, and the other bags are empty. The blood-collecting bag is formed of flexible polyvinylchloride. The blood-collecting bag is autoclaved after containing anticoagulant. The other bags are formed of polyolefin such as EVA, and radiation- or gas-sterilized in an empty state.

10 Claims, 3 Drawing Sheets

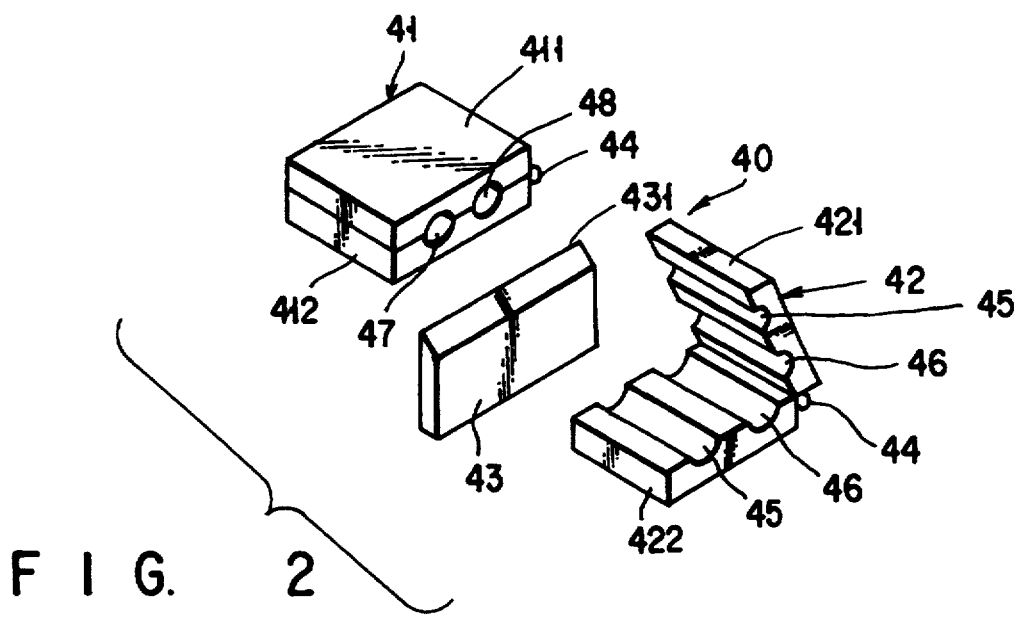
F I G. 2
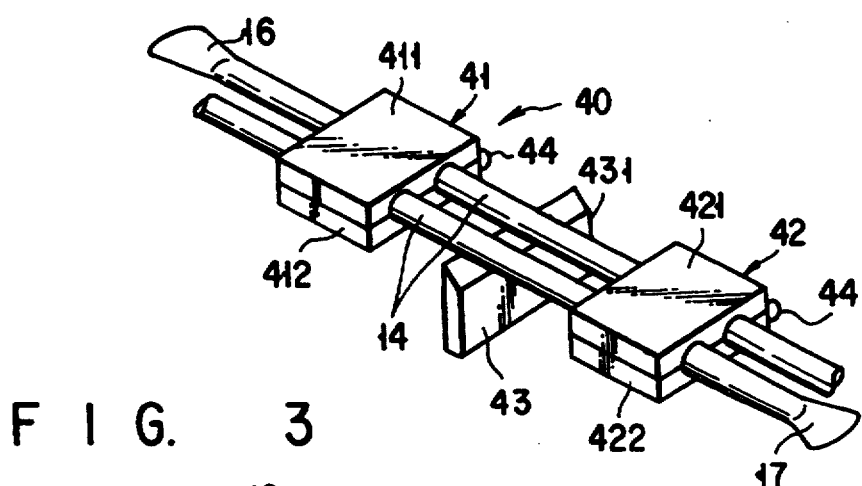
F I G. 3
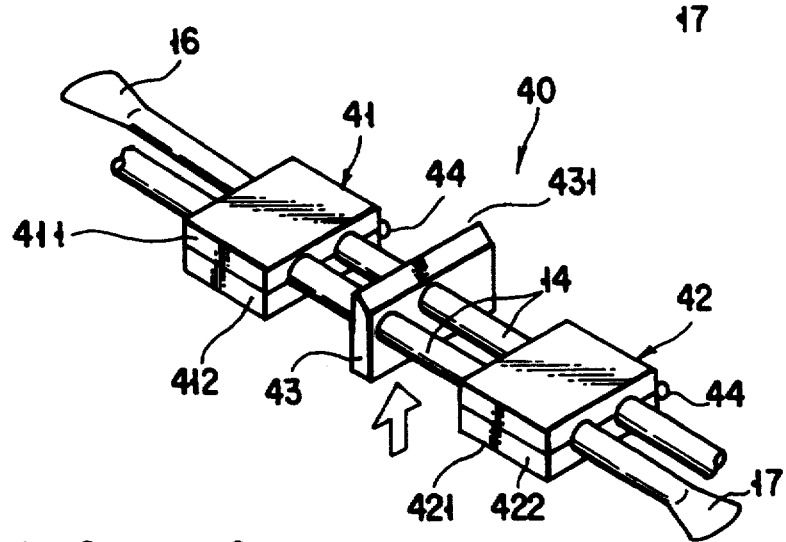
F I G. 4

MEDICAL CONTAINER DEVICE AND METHOD FOR MANUFACTURING SAME

BACKGROUND OF THE INVENTION

1. Field of the Invention

The present invention relates to a medical container device having a plurality of bags containing blood and its components, and a method for manufacturing the same.

2. Description of the Related Art

In blood transfusion, for effective use of blood and reduction of an acceptor's load, there has been recently carried out a system in which blood withdrawn from a donor is separated into components by centrifugation or the like and only the components necessary to an acceptor are transfused. By the introduction of the component transfusion, blood has been effectively used as compared with the conventional whole blood transfusion.

In the above component transfusion, a container device (multiple bag) comprises a blood-collecting bag and one or more other bags.

Among the multiple bag, for example, a triple bag consists of the blood-collecting bag, a platelet conserving bag (hereinafter called PC bag) and a plasma conserving bag (hereinafter called plasma bag) which are connected to each other by a tube. Blood collected in the blood-collecting bag is separated into three components, that is, erythrocyte, platelet rich and platelet poor plasma by at least one centrifugal separation (PRP method). Then, these components are contained and conserved in the blood-collecting bag, PC bag, and plasma conserving bag, respectively.

Each bag of such a multiple bag is formed by overlying sheets made of flexible polyvinylchloride and fusing the edge portions. The reason why the sheet material of flexible polyvinylchloride is used is that a sheet made of the material has suitable permeability, suitable preservation of cells such as hemocyte and blood platelet, high heat resistance to autoclaving, and flexibility that bears a centrifuging operation, as well as easy fusion-bonding, easy manufacturing, and low cost of material. Particularly, regarding the blood-collecting bag, there is an advantage in that plasticizer (DEHP and the like) is suitably eluted from the sheet material, and conservation or preservation of erythrocyte in the blood-collecting bag is improved.

However, regarding the PC bag and the plasma bag, the use of a sheet made of flexible polyvinylchloride has the following disadvantages:

Regarding the PC bag, unless the capacity (surface area) of the bag is enlarged or the thickness of the sheet is small, sufficient oxygen and carbon dioxide permeability cannot be obtained, so that the preservation of blood platelet is worsened. Moreover, the plasticizer eluted from the sheet material exerts unfavorable influence on blood platelets. In other words, an activation index (low osmotic pressure shock recovery factor and aggregation) of blood platelet in vitro is lowered.

Moreover, plasma in the plasma bag is normally frozen and preserved. However, the strength of flexible polyvinylchloride is originally low at a low temperature. If there is a shock such as dropping of the plasma bag in a frozen state, fragile breakage is generated in the plasma bag.

In order to solve the above problems, U.S. Pat. No. 4,222,379 discloses a container device wherein the material of the PC bag or plasma bag is different from that of the blood-collecting bag.

However, since the whole body of such a container device is autoclaved, the material of the PC bag and plasma bag must have heat resistance that can resist autoclaving in addition to the above-required properties. Due to this, there is a disadvantage in that the selection of the material is limited. For example, in the case that ethylene-vinyl acetate copolymer (hereinafter called EVA) is used, crosslinking thereof must be performed by radioactive irradiation or a chemical method using peroxide or the like in order to obtain heat resistance that can resist autoclaving (110° C. or more).

Placing emphasis on the above-mentioned heat resistance, various properties necessary to the PC bag, the plasma bag, for example, flexibility, transparency, strength at low temperature, facility of manufacture, economical advantage, or safety, are lost.

SUMMARY OF THE INVENTION

It is an object of the present invention to provide a container device and its manufacturing method wherein material of bags can be selected without placing emphasis on heat resistance by improving a sterilizing method, so that various properties necessary to each bag can be improved.

The above object can be attained by a device and a method according to the present invention explained below.

According to a first aspect of the present invention, there is provided a medical container device comprising a first bag containing chemicals, formed of flexible polyvinylchloride, and subjected to a high pressure steam sterilization, an empty second bag formed of material different from the first bag, and subjected to a radiation- or gas-sterilization, and a first tube connecting the first bag to the second bag.

According to a second aspect of the present invention, there is provided a method for manufacturing a medical container device comprising steps of forming a first bag made of flexible polyvinylchloride, connecting a first tube element to the first bag, introducing chemicals in the first bag, sealing the first bag, subjecting the first bag containing chemicals to a high pressure steam sterilization, forming a second bag made of material different from flexible polyvinylchloride, connecting a second tube element to the second bag, sealing the second bag in an empty state, subjecting the second bag to a radiation-or gas-sterilization, and connecting the first and second tube elements in a sterile state to form a first tube for connecting the first and second bags.

In a preferable specific form, the second bag is formed of polyolefin or polymer alloy containing polyolefin. The material of the first and second tube elements has the same composition or compatibility. The sterile connection between the first and second tube elements is made by cutting the end portions of the tube elements to be connected while heating, and fusion-bonding the cut end portions.

In the preferable specific form, the second tube connected to the first bag, and a blood-collecting needle connected to the second tube are further included, and the first bag is used as a blood-collecting bag. In this case, for example, anticoagulant used for blood is used as chemicals.

According to the present invention, a bag containing chemicals and an empty bag are subjected to different sterilizing methods, so that material of bags can be widely selected without considering the condition restricted by the sterilizing method such as heat resistance to autoclaving.

As a result, various properties necessary to the respective bags, for example, flexibility, transparency, gas permeability, strength at low temperature, safety, and the like can be improved.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 2 is a perspective view showing heat connection means for connecting a tube;

FIG. 3 is a perspective view showing a step of a tube connection process using the heat connection means of FIG. 2;

FIG. 4 is a perspective view showing a step of the tube connection process, following the step of FIG. 3;

DETAILED DESCRIPTION OF THE PREFERRED EMBODIMENTS

Figure 1:
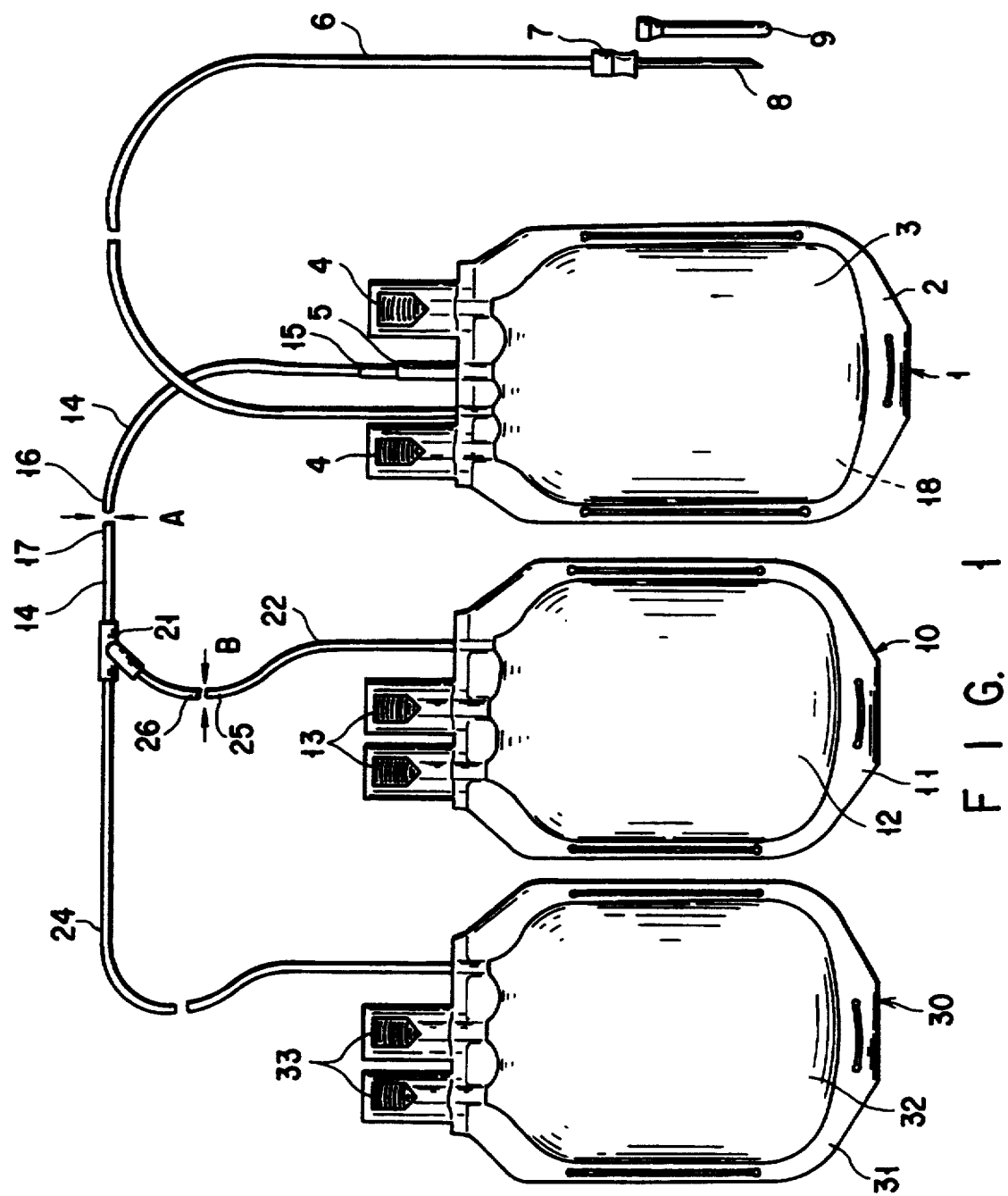
FIG. 1 is a plane view showing an embodiment of a container device of the present invention

The container device of the present invention and its manufacturing device will be explained based on a preferred embodiment shown in the drawings attached hereto.

FIG. 1 is a plane view showing the structure of a medical container device of the present invention. As shown in the figure, a container device 1 is a triple bag comprising a blood-collecting bag, a PC bag, and a plasma bag, which are respectively connected through tubes.

The blood-collecting bag 1 positioned at the right side of FIG. 1 is formed by overlying resin-made sheets (to be explained later) having flexibility, and fusion-bonding (thermofusing, high frequency fusing) or adhering the edges of the sheets at a sealing section 2 so as to obtain a bag-like shape.

In an inside portion enclosed with the sealing section 2, there is formed a blood component containing section 3 containing collected blood and rich erythrocyte obtained from the blood by centrifugal separation.

Two openings 4, 4 having a peel tab are formed on the upper portion of the blood-collecting bag, and a discharge port 5 for connecting the bag 1 to the other bags is formed between two openings.

One end of a tube 14 is connected to the discharge port 5 through a connecting member 15.

A branching connector 21 branching into two ways is connected to the other end of the tube 14. In a connecting member 15, there is preferably used a fragile member by which a channel is closed before the fragile member is broken and the channel is opened after the fragile member is broken. More specifically, "Clip Chip (Trade Name)" produced by Terumo Corporation can be used. In the present invention, the connecting member 15 may not be provided, and the tube 14 is preferably closed and opened suitably by a clamp.

Moreover, one end of a tube 6 having flexibility is connected to the upper portion of the blood-collecting bag 1 so as to communicate with the blood component containing section 3. Then, a blood-collecting needle 8 is connected to the other end of the tube 6 through a hub 7. Moreover, a cap 9 is provided to the hub 7 so as to cover the blood-collecting needle 8.

A PC bag 10 positioned at the center of FIG. 1 is formed by overlying resin-made sheets (to be explained later) having flexibility, and fusion-bonding (thermofusing, high frequency fusing) or adhering the edges of the sheets at a sealing section 11 so as to obtain a bag-like shape.

In an inside portion enclosed with the sealing section 11, there is formed a blood platelet containing section 12 containing blood platelets separated from blood in the blood-collecting bag 1.

Two openings 13, 13 having a peel tab are formed on the upper portion of the PC bag 10.

Moreover, one end of a tube 22 communicating with the blood platelet containing section 12 and having flexibility is connected to the side portion of the openings 13 of the upper section of the bag 10. The other end of the tube 22 is connected to one branch end of the branching connector 21. Thereby, the blood component containing section 3 of the blood-collecting bag 1 and the blood platelet containing section 12 of the PC bag 10 communicate with each other through the tubes 14, 22, and the branching connector 21.

A plasma bag 30 positioned at the left side of FIG. 1 is formed by overlying resin-made sheets (to be explained later) having flexibility, and fusion-bonding (thermofusing, high frequency fusing) or adhering the edges of the sheets at a sealing section 31 so as to obtain a bag-like shape.

In an inside portion enclosed with the sealing section 31, there is formed a plasma containing section 32 containing plasma (particularly, platelet poor plasma) separated from blood.

Two openings 33, 33 having a peel tab are formed on the upper portion of the plasma bag 30.

Moreover, one end of a tube 24 communicating with the plasma containing section 32 and having flexibility is connected to the side portion of the openings 33 of the upper section of the bag 30. The other end of the tube 24 is connected to one branch end of the branching connector 21. Thereby, the plasma containing section 32 of the plasma bag 30, the blood component containing section 3 of the PC bag 10, and the blood platelet containing section 12 communicate with each other through the tubes 14, 22, 24 and the branching connector 21.

The branching connector 21 is formed of a resin material, for example, polyvinylchloride, polyethylene, polypropylene, polycarbonate, or the like.

In the above-mentioned container device, there are provided at least one bag containing chemicals (first bag) and at least one empty bag (second bag). For example, the unused PC bag 10 and plasma bag 30 are employed as empty bags, and chemicals such as an anticoagulant 18 is contained in the blood-collecting bag 1.

The sterilizing method of each bag is different depending on the bag containing chemicals or the empty bag. Moreover, the sheet material of each bag is different depending on the sterilizing method.

The blood-collecting bag 1 containing chemicals is subjected to a high pressure steam sterilization (autoclave sterilization). In this case, there is no specific limitation in the sterilizing condition. However, it is preferable that, for example, sterilizing time is about 5 to 60 minutes at a temperature of 110° to 135° C. and a steam partial pressure of 1.4 to 3.1 arm. Under this condition, the inside of the blood-collecting bag 1 and the anti-coagulating agent 18 are surely sterilized.

It is noted that a radiation sterilization (particularly, γ-ray sterilization) or a gas sterilization (particularly, ethylene oxide gas (EOG) sterilization) is not suitable to the bag containing chemicals. More specifically, since the γ ray does not pass through the chemicals, there is little sterilizing effect. EOG dissolves in the chemicals, and reacts with water and chlorine in the chemicals, thereby generating toxic ethylene glycol and ethylene chlorohydrin.

On the other hand, the empty bags, that is, PC bag 10 and plasma bag 30, are subjected to a radiation sterilization (particularly, γ-ray sterilization) or a gas sterilization (particularly, ethylene oxide gas (EOG) sterilization). In this case, there is no specific limitation in the sterilizing condition. However, the following conditions are preferably provided.

In the case of γ ray sterilization, the amount of γ ray radiation is preferably about 1 to 5 Mrad. In the case of EOG sterilization, EOG concentration is preferably about 500 to 800 mg/l, and gas contacting time is preferably about 90 to 240 minutes. Under these conditions, the insides of the PC bag 10 and the plasma bag 30 are surely sterilized.

Since the bags are empty, there is no problem even if such a radiation sterilization or a gas sterilization is performed. Also, the biggest advantage of the present invention lies in that sheet material of the bags does not need heat resistance to high sterilization temperature since the above autoclave sterilization is not performed.

In consideration of the heat resistance based on the above sterilizing method, the following sheet material of each of the bags 1, 10, and 30 is used.

The sheet material of the blood-collecting bag 1 is flexible polyvinylchloride. Flexible polyvinylchloride has heat resistance to autoclaving and flexibility bearing the centrifugal operation. Also, by use of flexible polyvinylchloride, working to the bag and the manufacture of the bag can be easily performed, and the cost of material is low.

As a plasticizer used for flexible polyvinylchloride, for example, di-(ethylhexyl) phthalate (DEHP), di-(n-decyl) phtalate (DnDP) or the like is used. Particularly, DEHP is preferably used since DEHP eluted from the sheet material generates a function of controlling hemolysis of erythrocyte in the blood-collecting bag 1, so that preservation of the erythrocyte is improved.

The content of plasticizer represented by DEHP is about 30 to 70 part by weight of 100 of polyvinylchloride.

The thickness of the sheet of the blood-collecting bag 1 is not particularly limited. However, the thickness of about 0.2 to 0.65 mm, particularly about 0.30 to 0.50 mm, is preferably set.

The capacity of the blood-collecting bag 1 is not particularly limited. However, the capacity of about 100 to 600 ml, particularly about 200 to 500 ml, is preferably set.

The sheet material of the PC bag 10 and plasma bag 30 is different from that of the blood-collecting bag 1. Moreover, the sheet material of the PC bag 10 and plasma bag 30 does not need heat resistance to autoclaving which results in melting, softening, change of property, and deterioration of the sheet material. More specifically, for example, polyester such as polyethylene terephtalate (PET) or polybutylene terephtatate (PBT), polyvinylidene chloride, silicone, various polyolefin, or arbitrary combination of these materials (for example, lamination) may be used. Particularly, polyolefin is preferably used since polyolefin has flexibility and transparency. Also, polyolefin has high strength at low temperature. For example, when plasma is contained and frozen in the plasma bag 30, a high-impact resistance can be obtained.

As polyolefin, olefin such as ethylene, propylene, butadiene, isoprene, or a polymer in which diolefin is polymerized, copolymerized, or ionic-copolymerized, is used. For example, high pressure processed polyethylene, linear low density polyethylene (LLDPE), polypropylene, EVA (crosslinked or uncrosslinked EVA), styrene-elastomer, or arbitrary combinations of these matters is used. Particularly, EVA, specially, uncrosslinked EVA is favorably used in view of the point that flexibility, transparency, and workablity are excellent.

Moreover, since the uncrosslinked EVA does not need processing means for crosslink, the uncrosslinked EVA has advantages over the crosslinked EVA from an economical viewpoint. Also, the uncrosslinked EVA is excellent in safety. In other words, there is no problem in that various decomposition products generated by crosslink processing and peroxide used for crosslink exert unfavorable influence on blood preparation preserved in the bag.

Moreover, polymer-blended material which is formed by mixing such polyolefin, particularly, EVA with one of various types of thermoplastic resin or thermoplastic elastomer, and graft polymer, and block polymer can be used.

Furthermore, the sheet of the PC bag 10 and the plasma bag 30 can be formed of a lamination having two or more layers (for example, laminated film). In this case, at least one layer can be formed of the above-explained material. In the case that a high pressure steam sterilization is performed on the bag, all layers forming the lamination must have heat resistance resisting to the treatment. However, since a high pressure steam sterilization is not performed on the PC bag 10 and the plasma 30, material having no heat resistance can be used in each layer of the lamination, the pattern of the layer structure and its variation can be widened in designing and manufacturing the lamination.

In the case that such sheet is formed of the lamination, the lamination preferably has a layer formed of polyolefin (particularly, EVA) or polymer alloy containing polyolefin. The thickness of the layer preferably accounts for 40% or more of the whole thickness of the sheet, particularly 60%.

The thickness of the sheet of PC bag 10 is not particularly limited. However, the thickness of about 0.1 to 0.5 mm, particularly about 0.15 to 0.30 mm, is preferably set.

The thickness of the sheet of plasma bag 30 is not particularly limited. However, the thickness of about 0.2 to 0.6 mm, particularly about 0.20 to 0.35 mm, is preferably set.

The amount of permeating oxygen gas of PC bag 10 is set to about 1000 to 20000 ml/$m^2$.day.atm (30° C.). preferably about 2000 to 15000 ml/$m^2$.day.atm (30° C.).

The amount of permeating carbon dioxide gas of PC bag 10 is set to about 2000 to 50000 ml/$m^2$.day.atm 30° C.), preferably about 5000 to 30000 ml/$m^2$.day.atm (30° C.).

The plasma bag 30 having a high-impact resistance at a low temperature is preferably used. For example, there is preferably used a plasma bag having an impact resistance to the extent that no breakage occurs in the bag even if the plasma bag 30, which is frozen at a temperature of −40° C., is dropped from a place having height of about 1 m.

The capacity of PC bag 10 and that of plasma bag 30 are not particularly limited. However, the capacity of each bag is set to preferably about 100 to 600 ml, particularly about 150 to 500 ml.

It is noted that the PC bag 10 and plasma bag 30 may have the same or different type of the sheet material, the thickness of the sheet, the amount of permeating gas, and the capacity.

In the container device shown in FIG. 1, regarding the material of the tubes 6, 14, 22, and 24, there can be used polyvinylchloride, polyethylene, polypropylene, polyester such as PET or PBT, EVA, polyurethane, polyester elastomer, and thermoplastic elastomer such as styrene-butadiene-styrene copolymer. Particularly, polyvinylchloride is preferably used. If each tube is formed of polyvinylchloride, sufficient flexibility and elasticity can be obtained, so that the treatment of the tubes can be easily performed, and such tubes are suitable for the closing operation using the clamp.

In a case that tubes 22 and 24 are formed of polyvinylchloride, the PC bag 10 and plasma bag 30 are formed of a different material. However, if two-layer tube disclosed in Published Unexamined Japanese Patent Application No. 02-1280 is applied to the tubes 22 and 24, high adhesion between the bags 10, 30 and the tubes 22, 24 can be obtained.

The inner diameter of each of tubes 6, 14, 22, and 24 is not particularly limited. However, the diameter of about 2.0 to 4.5 is preferably set.

Regarding the tubes 6, 14, 22 and 24 other than the use of a single tube, a plurality of tubes may be used and connected to each other by a tube connection member such as a connector. Or, these tubes may be connected to each other by a sterile connection method to be explained later. Thereby, he respective bags 1, 10, and 30 can be easily separated from each other in steps of sterilizing each bag, preserving blood components, centrifugal-separating blood, and performing other preparation working.

The anticoagulant 18 is normally liquid. For example, ACD solution, CPD solution, CPDA-1 solution, sodium heparin solution may be used. These liquids are aqueous solutions containing components shown in Table 1.

TABLE 1

| Anticoagulant | Components | |
|---|---|---|
| ACD solution | sodium citrate | 2.20% |
| | citric acid | 0.80% |
| | glucose | 2.20% |
| CPD solution | sodium citrate | 2.63% |
| | citric acid | 0.327% |
| | glucose | 2.32% |
| | phosphoric acid.1.sodium | 0.251% |
| CPDA-1 solution | sodium citrate | 2.63% |
| | citric acid | 0.327% |
| | glucose | 2.9% |
| | phosphoric acid.1.sodium | 0.251% |
| | adenine | 0.0275% |
| Heparin | sodium chloride | 0.9% |
| | sodium heparin | 1000U/30 ml |

The appropriate amount of these anticoagulants is ACD solution of about 30 ml, sodium heparin solution of about 30 ml, CPD solution of about 28 ml, and CPDA-1 solution of about 28 ml in relation to the whole human blood of 200 ml.

A method of manufacturing the container device of the present invention will be explained.

First of all, the bag 1 is formed of soft polyvinylchloride. Then, the bags 10 and 30 are formed of a different material such as polyolefin resin. Chemicals 18 are contained in the bag 1, and the bag is sealed. The bags 10 and 30 are sealed in an empty sate. The bag 1 containing chemicals 18 is subjected to a high pressure steam sterilization and the empty bags 10 and 30 are subjected to a radiation- or gas-sterilization. Thereafter, the tubes of the respective bags are connected to each other in a sterile state. Thereby, a container device can be manufactured.

As a method for connecting end portions 16 and 17 of parts of the tube 14 in a sterile state, there may be used a method using a heat connection means 40.

FIG. 2 is a perspective view showing the structure of the heat connection means 40. FIGS. 3 to 6 are perspective views showing the connection processes of parts of the tube 14 by use of heat connection means 40. As shown in these figures, heat connection means 40 is structured such that a wafer 43 is formed between a pair of holders 41 and 42. In the connection of the tube 14, parts of the tubes 14 are stretched between the holders 41 and 42 to overlap each other in length. The parts of the tube 14 are cut by the heated wafer 43 and fused. Then, one holder 41 is moved, and the wafer 43 is removed, and the parts of the tube 14 are bonded to each other.

More specifically, the holders 41 and 42 respectively comprise holder pieces 411, 412 and 421 and 422, which are divided into upper and lower parts. These holder pieces 411, 412, 421, 422 are respectively rotatable by hinges 44.

There are formed two grooves 45 and 46 whose cross sections are semicircular in the opposite surfaces of the holder pieces 411, 412 and 421 and 422, respectively. Then, tube holding sections 47 and 48 each having a circular cross section are formed in a state that the holder pieces 411, 412 and 421 and 422 are placed one upon another, respectively.

As material of the holder pieces 411, 412, 421, 422, there are various types of thermoplastic resin or thermosetting resin, various types of ceramic such as alumina, silica, and various types of metals such as stainless, aluminum, and the like.

The wafer 43 is formed of, various types of metals, for example, iron, copper, aluminum, gold, silver, titan, or alloy containing these metals. A sharp edge 431 is formed on the end portion of the side first contacting the tube 14.

The following will explain the method for using heat connection means 40.

As shown in FIG. 3, the cut portions 16 and 17 of the parts of the tube 14 are overlapped in parallel by a predetermined length to be opposed to each other, and placed in the grooves 45 and 46 of the holders 41 and 42. Then, the holder pieces 411, 412 and 421 and 422 are closed, respectively, and the two parts of the tube 14 are sandwiched between the tube holding sections 47 and 48, and fixed thereto.

As shown in FIG. 4, the wafer 43 is heated to the temperature which is higher than the melting point of the tube 14. Then, the parts 14 supported in parallel are cut by the edge 431, and the cut portions of the parts 14 are melted by the heat of the wafer 43. At this time, since the cut portions of the parts of the tube 14 are in a state that these portions are melted or softened, the sterilization state is maintained by heat of the wafer 43.

Figure 5:
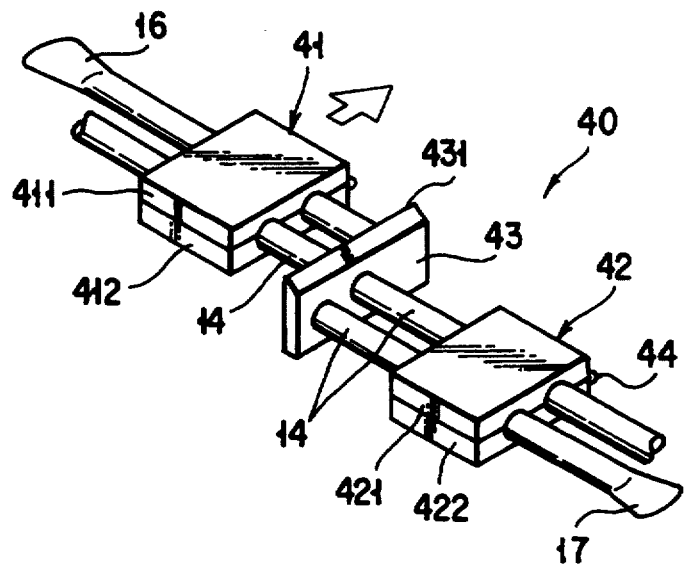
FIG. 5 is a perspective view showing a step of the tube connection process, following the step of FIG. 4.

As shown in FIG. 5, one holder 41 is moved in the direction where the tubes are arranged side by side (direction of an arrow of the figure) as the melting state of the cut portions of the parts 14 are maintained, and then the holder 41 is stopped and fixed such that the cut sections of the parts 14 are opposite to each other.

Figure 6:
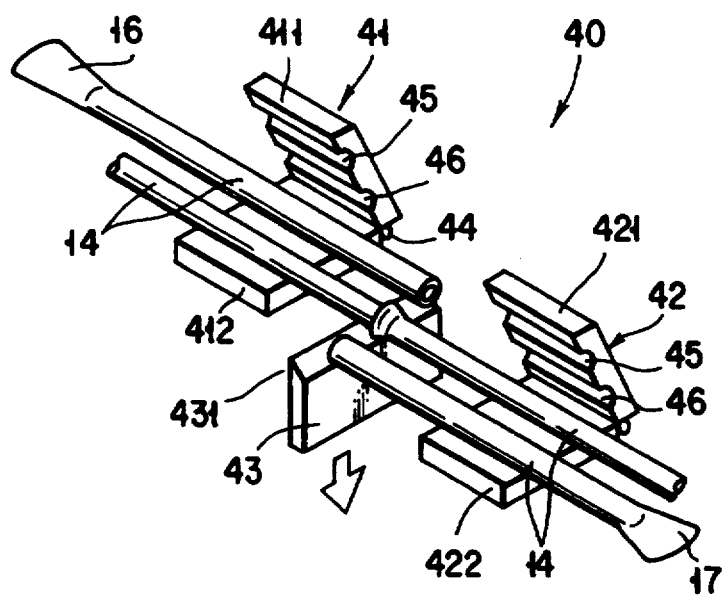
FIG. 6 is a perspective view showing a step of the tube connection process, following the step of FIG. 5.

As shown in FIG. 6, the wafer 43 is pulled out at right angles to the tubes 14, and one holder 41 is pressed to the other holder 42. Thereby, the cut portions of the melted tubes 14 are adhered to each other. Even in this connection of the tubes 14, the sterilization state is also maintained by heat of the wafer 43.

The tube pieces including the cut portions 16 and 17 are removed. The materials of the tubes are not limited to materials having the same composition, but materials having compatibility may be used.

It is noted that the method for connecting the tubes 14 in the sterile state is not limited to the method using heat connection means 40. For example, a method employing another connector utilizing heat may be used.

According to the manufacturing method of the container device of the present invention, the blood-collecting bag 1 formed of flexible polyvinylchloride and the PC bag 10 and plasma bag 30, which are made of an other material, can be easily sterilized by the different methods. Therefore, the sterilization can be performed under optimum conditions considering the point whether or not chemicals are contained.

Particularly, as Example 2 to be explained later, since the PC bag 10 and plasma bag 30 can be independently sterilized, the sterilization method and sterilization conditions can be suitably selected for each bag, so that sterilization can be suitably performed. Therefore, this method can be advantageously used in the case that the PC bag 10 is different from the plasma bag 30 in the sheet material, the thickness of the sheet, the capacities of the bags.

The above embodiment explained the case that the anticoagulant 18 is used as chemicals. However, the chemicals are not limited to the anticoagulant 18. For example, erythrocyte preservation liquid may be used. As erythrocyte preservation liquid, for example, there may be used SAGM solution, which is aqueous solution containing sodium choride: 0.877%, adenine: 0.0169%, glucose: 0.818%, and D-mannitol: 0.525%.

The above embodiment explained the case that the triple bag is used as the container device of the present invention. However, the present invention is not limited to the triple bag shown in the drawings. For example, there may be used a triple bag whose usage is different from the above-explained triple bag, a double bag in which the blood-collecting bag and the plasma bag are connected, or a bag in which one or two or more bags such as a cryoprecipitate (AHF) collecting bag or a leukocyte removing bag is/are added to such a double bag or triple bag.

Moreover, according to the present invention, in the case that a plurality of empty bags are used, a radiation- or gas-sterilization is not always provided to all bags, and at least one bag among these bags is formed of flexible polyvinylchloride, and the radiation- or gas-sterilization may be provided to the bag.

The following will explain the specific examples of the present invention.

EXAMPLE 1

The blood-collecting bag 1 shown in FIG. 1 was formed of sheet, which had a thickness of 0.40 mm and which was made of flexible polyvinylchloride suitable for erythrocyte preservation. The tubes 6 and 14 made of flexible polyvinylchloride were connected to the blood-collecting bag 1. The size of the blood-collecting bag was the same as that of the container device for collecting blood of 400 ml which was put on the market (the sizes of all bags described below are the same). Also, the blood-collecting needle 8 was connected to the tube 6.

The tube 14 was cut at a portion A of FIG. 1, and the end portion 16 was fusion-bonded, and sealed by a tube sealer (SEBRA (Trade Name), tube sealer model 1090 produced by ERA Co.). Thereafter, the blood component containing section 3 of the blood-collecting bag 1 was filled with CPD solution of 56 ml introduced through the blood-collecting needle 8 and the tube 6 and sealed with the cap 9, and subjected to a high pressure steam sterilization at a temperature of 121° C. for 20 minutes.

On the other hand, the PC bag 10 and plasma bag 30 were formed of a sheet having a thickness of 0.25 mm. The sheet was made of uncrosslinked EVA (containing vinyl acetate of 15% by weight), which is suitable for preserving blood platelet because of high gas permeability, and for freezing and preserving plasma because of high-impact resistance at low temperature. The sheet was obtained by extruding and molding the uncrosslinked EVA. These bags were connected to each other by the tubes 22 and 24 made of flexible polyvinylchloride and the branch connector 21. Thereby, the connecting body of the PC bag 10 and plasma bag 30 was prepared.

The tube 14 was cut at the portion A of FIG. 1, and the end portion 17 was fusion-bonded, and sealed by the tube sealer mentioned above.

Then, the connecting body was EOG-sterilized under the conditions of EOG concentration of 600 mg/l and sterilization time of 150 minutes.

The blood-collecting bag 1 and the connecting body of the PC bag 10 and plasma bag 30, which were individually sterilized, were connected to each other at the position close to the end portions 16 and 17 of tube parts 14 by heat connection means 40, so that the tube parts 14 communicated with each other. Thereby, the container device of the present invention comprising the blood-collecting bag 1, PC bag 10 and plasma bag 30 was obtained.

Comparative Example 1

Similar to Example 1, the blood-collecting bag 1 was prepared, and the tubes 6 and 14 were connected, and the blood-collecting bag 1 was filled with CPD liquid of 56 ml, and sealed. Also, similar to Example 1, the connecting body of the PC bag 10 and plasma bag 30 was prepared. Moreover, the blood-collecting bag 1 and the connecting body of the PC bag 10 and plasma bag 30 were connected to each other by heat connection means 40, so that they communicated with each other. Thereby, the container device comprising the blood-collecting bag 1, PC bag 10 and plasma bag 30 was obtained.

The above-obtained container device was subjected to the high pressure steam sterilization at a temperature of 121° C. for 20 minutes.

EXAMPLE 2

Similar to Example 1, the blood-collecting bag 1 was prepared and the tube 6, the blood-collecting needle 8 and the tube 14 were connected to each other, and the blood-collecting bag 1 was filled with ACD liquid of 60 ml, and sealed. The blood-collecting bag 1 was subjected to the high pressure steam sterilization at a temperature of 121° C. for 20 minutes.

Also, the PC bag 10 shown in FIG. 1 was formed of sheet having a thickness of 0.1 mm. The sheet was made of LLDPE, which is suitable for preserving blood platelet because of high gas permeability. Then, the PC bag 10 was connected to the tube 22 made of flexible polyvinylchloride and the branch connector 21. The tube 22 was cut at a portion B of FIG. 1, and the end portion 25 was fusion-bonded, and sealed by the tube sealer mentioned above.

Then, the PC bag 10 was γ ray-sterilized by the amount of radiation of 2 Mrad.

Next, similar to Example 1, the plasma bag 30 was prepared and connected to the tube 24. The end portion 17 of the tube 14 cut at the portion A of FIG. 1 and the end portion 26 of the tube 22 cut at the portion B were fusion-bonded, and sealed by the tube sealer mentioned above.

Then, the blood bag 30 was EOG-sterilized under the same conditions as Example 1.

The blood-collecting bag 1, PC bag 10, and plasma bag 30, which were individually sterilized, were connected to each other at the position close to the end portions 16 and 17 of the tube 14, and the end portions 25 and 26 of the tube 22 by heat connection means 40, so that the tubes 14 and 22 communicated with each other. Thereby, the container device of the present invention comprising the blood-collecting bag 1, PC bag 10 and plasma bag 30 was obtained.

Comparative Example 2

Similar to Example 2, the blood-collecting bag 1 was prepared, and the tubes 6 and 14 were connected, and the blood-collecting bag 1 was filled with ACD liquid of 60 ml, and sealed. Also, similar to Example 2, the PC bag 10 and plasma bag 30 were prepared. Moreover, similar to Example 2, these bags were connected to each other by heat connection means 40, so that they communicated with each other. Thereby, the container device comprising the blood-collecting bag 1, PC bag 10 and plasma bag 30 was obtained.

The above-obtained container device was subjected to the high pressure steam sterilization at a temperature of 121° C. for 20 minutes.

Experiment 1

Regarding each container device of Examples 1 and 2, a visual inspection, a function test, and a sterilization test were conducted based on the following method. As a result, the container devices of Examples 1 and 2 had good results of the visual inspection and the function test. Also, the sterilization of each inside of of the respective bags and tubes was maintained.

Regarding each container device of Comparative Examples 1 and 2, the same visual inspection and the function test were conducted. As a result, in both container devices of Comparative Examples 1 and 2, the PC bag 10 and the plasma bag 30 were deformed by heat of the high pressure steam sterilization and these bags were not able to contain platelet rich plasma (PC) and platelet poor plasma (PPP), and it was impossible to use these bags.

[Method for tests]

1. Visual Inspection

The container device was observed with eyes so as to confirm whether or not there was abnormality which might generate trouble in using the device.

2. Function Test

The blood-collecting bag was filled with pseudo blood of about 40 ml, which is provided in the standard of blood sets made of polyvinylchloride resin. The pseudo blood was moved to the PC bag and plasma bag. Then, it was confirmed that the pseudo blood was moved without stagnancy.

3. Sterilization Test

The anticoagulant in the blood-collecting bag was moved to the PC bag and plasma bag. The inner surface of each bag was washed with the anticoagulant. Thereafter, the anticoagulant was returned to the blood-collecting bag. The sterilization test of the anti-coagulant was conducted by an indirect method (membrane filter method), which is provided in the sterilization test of the general testing method according to the Japanese pharmacopoeia.

Comparative Example 3

The blood-collecting bag 1 shown in FIG. 1, PC bag 10, and plasma bag 30 were formed of a flexible polyvinylchloride sheet (having a thickness of 0.40 mm). These bags were connected to each other by the tubes 14, 22, 24 and the branch connector 21, thereby the container device was obtained. The blood-collecting bag 1 was filled with CPD liquid of 60 ml and sealed. Then, the container device was subjected to the high pressure steam sterilization at a temperature of 121° C. for 20 minutes.

Experiment 2

Regarding each container device of Example 1 and Comparative Example 3, the high-impact resistance under a low temperature was examined. First, human blood of 400 ml was collected in the blood-collecting bag of each container device. The collected blood was separated into three components, that is, erythrocyte rich component (CRC), PC, and PPP. Then, PPP of about 160 mm was moved to the plasma bag 30, and frozen in a freezing chamber of −40° C.

The plasma bag 30 of Example 1 was dropped on a concrete floor from the height of 2 m, and no breakage occurred. However, the plasma bag 30 of comparison 3 was dropped on the concrete floor from the height of 0.5 m, and considerable breakage occurred.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A method for manufacturing a medical container device comprising the steps of:
   (a) forming a first device part including:
      (i) a first bag made of flexible polyvinylchloride, and defining a first sealed space therein,
      (ii) chemicals in said first space, and
      (iii) a first tube element connected to the first bag and being in communication with the first space, the first tube element being made of a synthetic resin material and having a sealed end;
   (b) subjecting said first device part to a high pressure steam sterilization;
   (c) forming a second device part including:
      (i) a second bag made of a synthetic resin material different from flexible polyvinylchloride, and defining a second sealed space therein which is empty, and
      (ii) a second tube element connected to the second bag and being in communication with the second space, the second tube element being made of a synthetic resin material and having a sealed end, the first and second tube elements being made from materials at least one of (i) having the same composition as each other and (ii) being compatible with each other;
   (d) subjecting said second device part to one of a radiation- and gas-sterilization;
   (e) cutting off the sealed ends of the first and second tube elements while heating the sealed ends, and fusion-bonding the cut portions of said first and second tube elements to connect them in a sterile state, thereby connecting the second device part to the first device part;
   wherein the first device part further comprises a blood-collecting needle connected to the first bag for communication with the first space, and the first bag is used as a blood-collecting bag;
   wherein said step of subjecting said first device part to a high pressure steam sterilization occurs when the needle is sealed; and
   (f) introducing the chemicals into the first space through the needle.

2. The method according to claim 1, wherein said chemicals include an anticoagulant used for blood.

3. The method according to claim 2, wherein the second device part further includes a third bag in communication with the second bag.

4. The method according to claim 3, wherein the second and third bags are each made from a material selected from the group consisting of polyolefin and a polymer alloy containing polyolefin.

5. A method for manufacturing a medical container device comprising the steps of:
   (a) forming a first device part including:
      (i) a first bag made of flexible polyvinylchloride, and defining a first sealed space therein,
      (ii) chemicals in said first space, and
      (iii) a first tube element connected to the first bag and being in communication with the first space, the first tube element being made of a synthetic resin material and having a sealed end;
   (b) subjecting said first device part to a high pressure steam sterilization;
   (c) forming a second device part including:
      (i) a second bag made of a synthetic resin material different from flexible polyvinylchloride, and defining a second sealed space therein which is empty, and
      (ii) a second tube element connected to the second bag and being in communication with the second space, the second tube element being made of a synthetic resin material and having a sealed end;
   (d) subjecting said second device part to one of a radiation- and gas-sterilization;
   (e) forming a third device part including:
      (i) a third bag made of a synthetic resin material different from flexible polyvinylchloride, and defining a third sealed space therein which is empty, and
      (ii) third and fourth tube elements connected to the third bag and being in communication with the third space, the third and fourth tube elements each being made of a synthetic resin material and having a sealed end, the first and third tube elements being made from materials at least one of (i) having the same composition as each other and (ii) being compatible with each other, and the second and fourth tube elements being made from materials at least one of (i) having the same composition as each other and (ii) being compatible with each other;
   (f) subjecting the third device part to the other of said radiation- and gas-sterilization;
   (g) cutting off the sealed ends of the first and third tube elements while heating the sealed ends, and fusion-bonding the cut portions of said first and third tube elements to connect them in a sterile state, thereby connecting the third device part to the first device part; and
   (h) cutting off the sealed ends of the second and fourth tube elements while heating the sealed ends, and fusion-bonding the cut portions of said second and fourth tube elements to connect them in a sterile state, thereby connecting the second device part to the first and third device parts;
   wherein the first device part comprises a blood-collecting needle connected to the first bag for communication with the first space, and the first bag is used as a blood-collecting bag;
   wherein said step of subjecting said first device part to a high pressure steam sterilization occurs when the needle is sealed; and
   (i) introducing the chemicals into the first space through the needle.

6. The method according to claim 5, wherein said chemicals include an anticoagulant used for blood.

7. The method according to claim 6, wherein the second and third bags are each made from a material selected from the group consisting of polyolefin and a polymer alloy containing polyolefin.

8. A medical container device comprising:
   (a) a first device part subjected to a high pressure steam sterilization, the first device part including:

(i) a first bag made of flexible polyvinylchloride, and defining a first sealed space therein, (ii) chemicals in said first space, and (iii) a first tube element connected to the first bag and being in communication with the first space, the first tube element being made of a synthetic resin material; and (b) a second device part subjected to one of a radiation-and gas-sterilization, the second device part including:

(i) a second bag made of a synthetic resin material different from flexible polyvinylchloride, and defining a second sealed space therein which is empty, and (ii) a second tube element connected to the second bag and being in communication with the second space, the second tube element being made of a synthetic resin material;

wherein the first and second tube elements are made from materials at least one of (i) having the same composition as each other and (ii) being compatible with each other, the first and second tube elements being connected by fusion-bonding in a sterile state such that the second device part is connected to the first device part;

wherein the first device part comprises a blood-collecting needle connected to the first bag for communication with the first space, and the first bag is used as a blood-collecting bag; and wherein said chemicals include an anticoagulant used for blood.

9. The device according to claim 8, wherein the second device part further includes a third bag in communication with the second bag.

10. The device according to claim 9, wherein the second and third bags are each made from a material selected from the group consisting of polyolefin and a polymer alloy containing polyolefin.

* * * * *